United States Patent
Cinbis et al.

(10) Patent No.: US 9,211,091 B2
(45) Date of Patent: *Dec. 15, 2015

(54) SYSTEM FOR IDENTIFYING THE LOCATION OF A DEVICE WITHIN A PATIENTS BODY IN ORDER TO LOCATE THE FOSSA OVALIS FOR TRANS-SEPTAL PROCEDURES

(71) Applicant: Medtronic Ablation Frontiers LLC, Minneapolis, MN (US)

(72) Inventors: Can Cinbis, Shoreview, MN (US); Xiaonan Shen, Shoreview, MN (US); Jonathan Kuhn, Ham Lake, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,315

(22) Filed: Nov. 25, 2014

(65) Prior Publication Data

US 2015/0080688 A1    Mar. 19, 2015

Related U.S. Application Data

(60) Division of application No. 13/731,162, filed on Dec. 31, 2012, now Pat. No. 8,923,950, which is a continuation of application No. 12/696,488, filed on Jan. 29, 2010, now Pat. No. 8,369,932.

(51) Int. Cl.
*A61B 5/00* (2006.01)
*A61B 5/1455* (2006.01)
(Continued)

(52) U.S. Cl.
CPC ........... *A61B 5/14552* (2013.01); *A61B 5/0044* (2013.01); *A61B 5/0075* (2013.01); *A61B 5/0084* (2013.01); *A61B 5/061* (2013.01);
(Continued)

(58) Field of Classification Search
CPC .................. A61B 19/54; A61B 2017/00061; A61B 2017/00243; A61B 2019/5206; A61B 2562/0242; A61B 5/0044; A61B 5/0075; A61B 5/0084; A61B 5/061; A61B 5/064; A61B 5/065; A61B 5/14552; A61B 5/1459; A61B 5/4887; A61B 5/68
See application file for complete search history.

(56) References Cited

U.S. PATENT DOCUMENTS

| | | |
|---|---|---|
| 4,803,992 A | 2/1989 | Lemelson |
| 5,331,950 A | 7/1994 | Wood, Sr. |
| 5,782,755 A | 7/1998 | Chance et al. |
| 6,591,144 B2 | 7/2003 | Pigott |
| 6,650,923 B1 | 11/2003 | Lesh et al. |

(Continued)

FOREIGN PATENT DOCUMENTS

| | | | |
|---|---|---|---|
| WO | 2007138552 A2 | 12/2007 | |
| WO | 2007147058 A2 | 12/2007 | |
| WO | 2008066911 A2 | 6/2008 | |

*Primary Examiner* — Ruth S Smith
(74) *Attorney, Agent, or Firm* — Christopher & Weisberg, P.A.

(57) ABSTRACT

A system and method for identifying the location of a medical device within a patient's body may be used to localize the fossa ovalis for trans-septal procedures. The systems and methods measure light reflected by tissues encountered by an optical array. An optical array detects characteristic wavelengths of tissues that are different distances from the optical array. The reflectance of different wavelengths of light at different distances from an optical array may be used to identify the types of tissue encountered, including oxygenated blood in the left atrium as detected from the right atrium through the fossa ovalis.

9 Claims, 8 Drawing Sheets

(51) Int. Cl.
*A61B 5/1459* (2006.01)
*A61B 5/06* (2006.01)
*A61B 19/00* (2006.01)
*A61B 17/00* (2006.01)

(52) U.S. Cl.
CPC ............... *A61B 5/064* (2013.01); *A61B 5/065* (2013.01); *A61B 5/1459* (2013.01); *A61B 5/4887* (2013.01); *A61B 5/6852* (2013.01); *A61B 5/72* (2013.01); *A61B 19/54* (2013.01); *A61B 2017/00061* (2013.01); *A61B 2017/00243* (2013.01); *A61B 2019/5206* (2013.01); *A61B 2562/0242* (2013.01)

(56) References Cited

U.S. PATENT DOCUMENTS

| | | | |
|---|---|---|---|
| 6,697,667 | B1 | 2/2004 | Lee et al. |
| 7,056,294 | B2 | 6/2006 | Khairkhahan et al. |
| 7,270,662 | B2 | 9/2007 | Visram et al. |
| 8,369,932 | B2 * | 2/2013 | Cinbis et al. ............ 600/424 |
| 2004/0167502 | A1 * | 8/2004 | Weckwerth et al. ........ 606/9 |
| 2007/0051379 | A1 | 3/2007 | Lash et al. |
| 2009/0156916 | A1 | 6/2009 | Wang et al. |
| 2009/0156921 | A1 | 6/2009 | Wang |
| 2009/0221921 | A1 | 9/2009 | Cottrell et al. |
| 2009/0259167 | A1 | 10/2009 | Sakamoto et al. |
| 2009/0285538 | A1 | 11/2009 | Marple |
| 2011/0270046 | A1 | 11/2011 | Paul et al. |

* cited by examiner

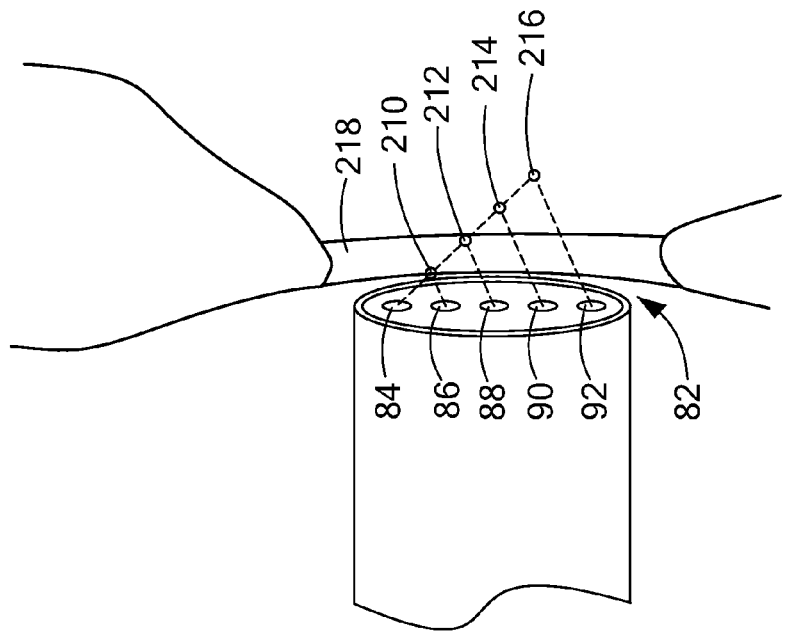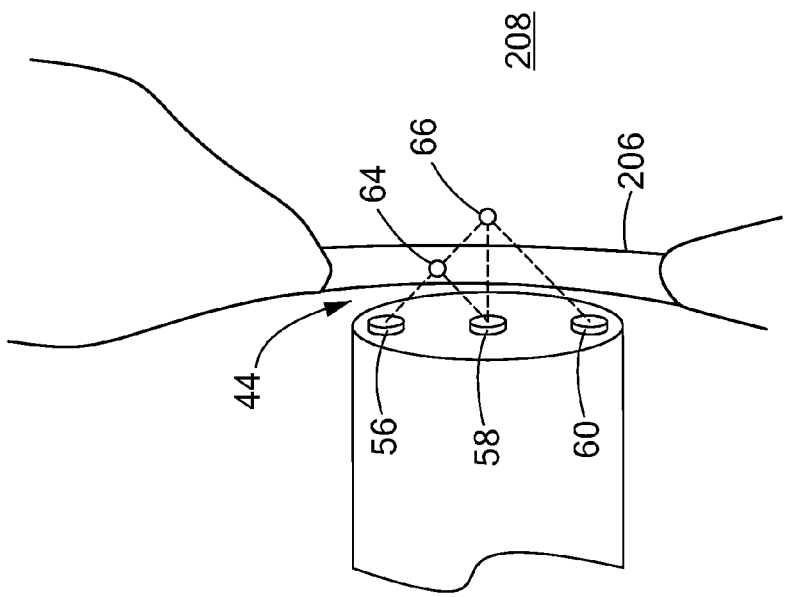

SYSTEM FOR IDENTIFYING THE LOCATION OF A DEVICE WITHIN A PATIENTS BODY IN ORDER TO LOCATE THE FOSSA OVALIS FOR TRANS-SEPTAL PROCEDURES

CROSS-REFERENCE TO RELATED APPLICATION

This application is a divisional of patent application Ser. No. 13/731,162, filed Dec. 31, 2012, entitled SYSTEM FOR IDENTIFYING THE LOCATION OF A DEVICE WITHIN A PATIENT'S BODY IN ORDER TO LOCATE THE FOSSA OVALIS FOR TRANS-SEPTAL PROCEDURES, which is now U.S. Pat. No. 8,923,950, issued Dec. 30, 2014, which is a continuation of patent application Ser. No. 12/696,488, filed Jan. 29, 2010, entitled OPTICAL METHODS OF IDENTIFYING THE LOCATION OF A MEDICAL DEVICE WITHIN A PATIENT'S BODY IN ORDER TO LOCATE THE FOSSA OVALIS FOR TRANS-SEPTAL PROCEDURES, which is now U.S. Pat. No. 8,369,932, issued Feb. 5, 2013, the entirety of all of which is incorporated herein by reference.

STATEMENT REGARDING FEDERALLY SPONSORED RESEARCH OR DEVELOPMENT n/a

FIELD OF THE INVENTION

The present invention relates to a system and method for optically identifying the position of a medical device within a patient, and particularly for using optical methods for identifying an optimal region of the interatrial septum of the heart for puncturing during a trans-septal procedure.

BACKGROUND OF THE INVENTION

Catheterization procedures have become the preferred methods for treating a variety of heart conditions. A catheter has a long, flexible body that may be introduced into the vasculature and guided into the heart or another organ of the body. By incorporating various medical devices, for example an ablation device, into the distal portion of a catheter, it may be used for ablation, as well as other procedures including angioplasty, dilation, biopsy and other procedures within the human heart and elsewhere.

For certain cardiovascular procedures, a catheter is inserted into an artery or vein in the leg, neck, torso or arm and threaded through the vasculature into the heart. FIG. 1 (prior art) shows a human heart 10 into which a catheter 12 has been introduced. In a common procedure, a catheter 12 enters into the right atrium 14 through the inferior vena cava 16. From the right atrium 14, the catheter may be directed to other regions of the heart.

Many procedures require introducing the catheter to the left atrium 18. One method of entering the left atrium 18, known as a trans-septal procedure, includes first entering the right atrium 14 through the vena cava 16 and then puncturing the interatrial septum 20. The interatrial septum 20 is the portion of the atrial wall which divides the left and right atria. Once the interatrial septum 20 is punctured, the end of the catheter 12 proceeds into the left atrium 18 where it may perform ablation or other medical treatments.

At the center of the interatrial septum 20 is a thin fibrous region known as the fossa ovalis 22. The fossa ovalis 22 is surrounded by the muscular tissue 24 of the atrial walls. The fossa ovalis 22 is relatively thin and does not include muscular tissue, making it the generally preferred region in which to puncture the interatrial septum during trans-septal procedures. Puncturing of the muscular tissue surrounding the fossa ovalis causes unwanted damage to the heart.

Accurate localization and identification of the fossa ovalis presents significant challenges. The fossa ovalis is invisible to current imaging techniques used to visualize a catheter during intercardial procedures, such as fluoroscopy. As a result, a physician must rely upon his own skill to position the tip of a catheter prior to puncturing the fossa ovalis.

Another difficulty encountered during trans-septal procedures is the variance in the thickness of the fossa ovalis between different individuals. Without knowing the approximate thickness of the fossa ovalis being punctured, a surgeon does not know how far a puncturing device on a catheter must travel or how much force is required in order to traverse the fossa ovalis. Thus an additional risk inherent in trans-septal procedures is that too much force will be applied to the catheter, resulting in piercing both the fossa ovalis and other structures within the heart such as the heart wall or aorta in unnecessary and undesirable locations.

One method of identifying the fossa ovalis uses spectroscopy and the ability of light to penetrate some thickness of tissue. The blood in the right atrium, where the catheter is introduced into the heart, is filled with deoxygenated blood that has a characteristic absorption spectrum 30 shown in FIG. 2. The absorption spectrum 30 of deoxygenated, right atrium blood differs significantly from the absorption spectrum 32 of the oxygenated blood found in the left atrium, particularly within the range of 600 nm to 805 nm. Because the fossa ovalis is very thin, the oxygenated blood of the left atrium may be viewed by an optical device abutting the fossa ovalis.

The fossa ovalis is the only region of the right atrium where oxygenated blood and its characteristic spectrum may be observed. Thus, a catheter may incorporate an optical device that illuminates the blood and tissue surrounding the catheter tip and detect the spectrum reflected back. When such an optical device detects the absorption spectrum of oxygenated blood, the device is abutting the fossa ovalis. Thus, by moving a catheter tip about the right atrium and particularly around the atrial wall of the right atrium, an operator of a catheter device may identify the fossa ovalis prior to puncturing the interatrial septum.

However, the nature of the optical device may create difficulties in accurately identifying the fossa ovalis. The light being reflected and observed by the detector must travel far enough to be reflected by the oxygenated blood of the left atrium. Where an optical device has an emitter for illuminating surrounding tissue and a detector for observing the absorption spectra positioned very close to each other, most of the observed reflected light is reflected from the fossa ovalis itself and not the oxygenated blood of the left atrium. Thus, the fossa ovalis may not be accurately localized.

If, on the other hand, the emitter and detector are relatively far apart, the detector may observe light reflected from the left atrium even though it traveled through the muscular wall, not the fossa ovalis. As a result, a portion of the interatrial septum having muscular tissue may be mistakenly identified as the fossa ovalis. Thus, a trans-septal puncture may be inadvertently made through muscular tissue, causing unnecessary damage.

It is therefore desirable to provide a system and method for identifying the location of a medical device within a patient and particularly for accurately identifying when a medical device is abutting the fossa ovalis. It is also desirable to be able to measure light reflected from different distances from the tip of the catheter within the body.

SUMMARY OF THE INVENTION

The present invention provides a method for identifying the location of a medical device within a patient. Light is emitted from an emitter toward at least one tissue within a body. The reflected light is measured by two or more receivers which are separated by different distances from the emitter. The measured reflected light may then be used to calculate a remittance value for two wavelengths at each of the receivers. A remittance ratio is then calculated by dividing the remittance values of the two wavelengths for each receiver. This may be done with wavelengths ranging between 600 nm and 1000 nm. Specific wavelengths 660 nm and 940 nm may be measured using this technique.

In addition, the slope of the remittance values over the wavelength range may be calculated for the light detected by each of the receivers. Optionally, the curvature over the range of wavelengths may be calculated to identify the characteristic spectra of oxygenated blood and other tissue. The emitter and receivers may be incorporated onto a face plate.

A medical device for identifying the location of a medical device within a patient's body includes an intravascular catheter and an optical array. The optical array has one or more emitters for emitting light and receivers for detecting reflected light, wherein the receivers are not all equidistant from the emitter. The medical device also includes a spectrometer in communication with the emitter and the receivers. The emitter and receivers may be on a face plate. The optical array may be inserted into a lumen in a catheter and protrude from a distal region of the catheter and have two face plates.

A face plate may be annular and surrounding an opening to a lumen in the catheter. The face plate may abut an interatrial septum and may be moved across the interatrial septum and detect light from a plurality of locations along the interatrial septum.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 13 is an enlarged view of the optical array of FIG. 4 abutting another interatrial septum; and FIG. 14 is an enlarged view of the optical array of FIG. 5 abutting a fossa ovalis.

DETAILED DESCRIPTION OF THE INVENTION

The present invention provides a system and methods of use thereof for characterizing the optical characteristics of tissue surrounding a medical device within a patient. In particular, the present invention provides a medical system and methods of use thereof for identification of a targeted tissue type.

Figure 1:
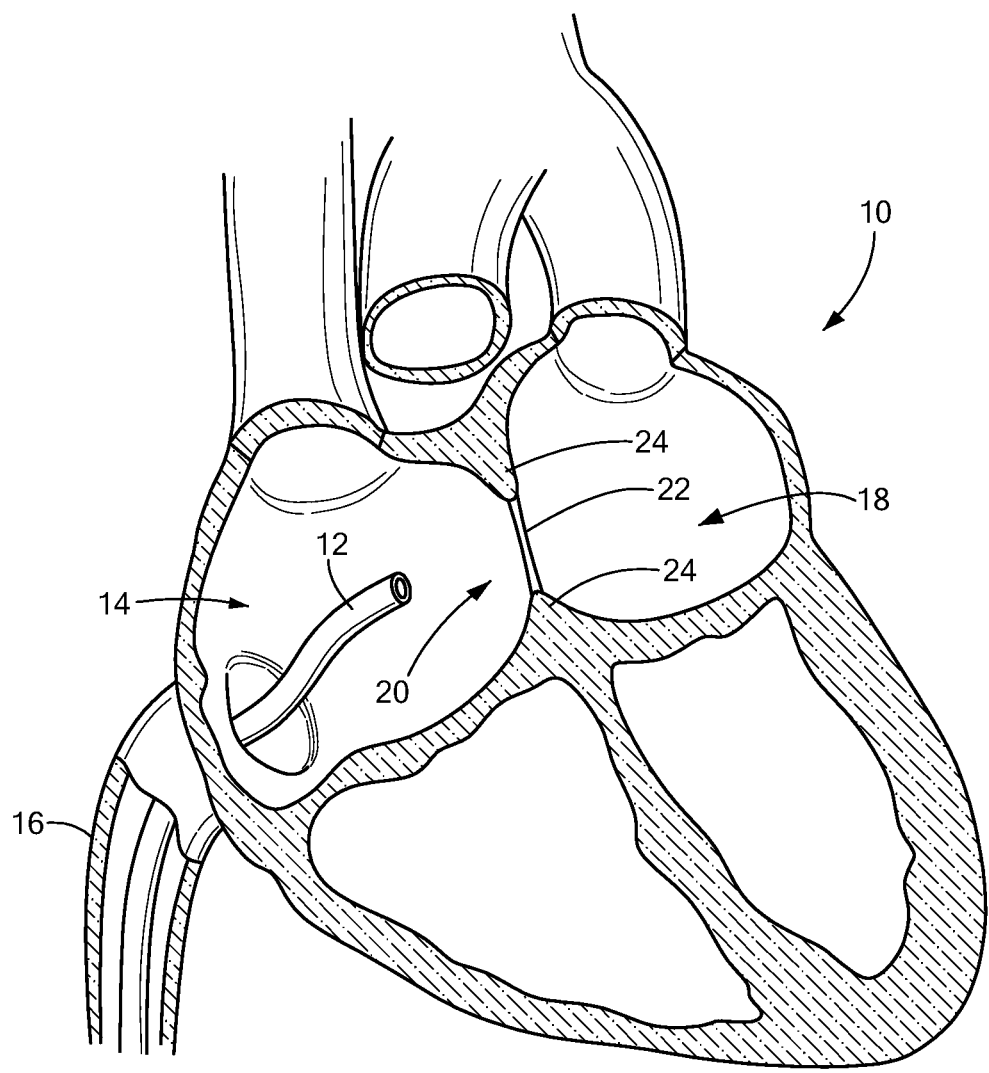
FIG. 1 is a view of a human heart having a catheter inserted into the right atrium.
Figure 2:
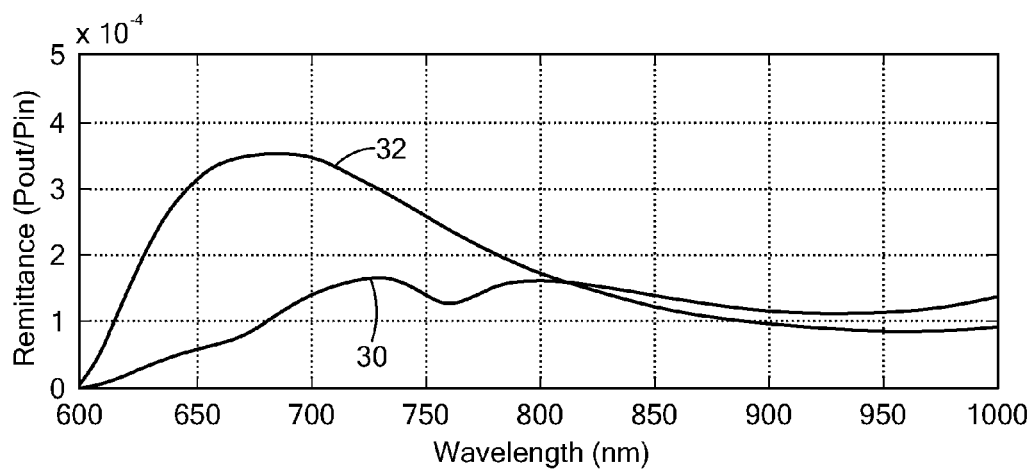
FIG. 2 is a graph of absorption spectra of various tissues found within the human heart.
Figure 3:
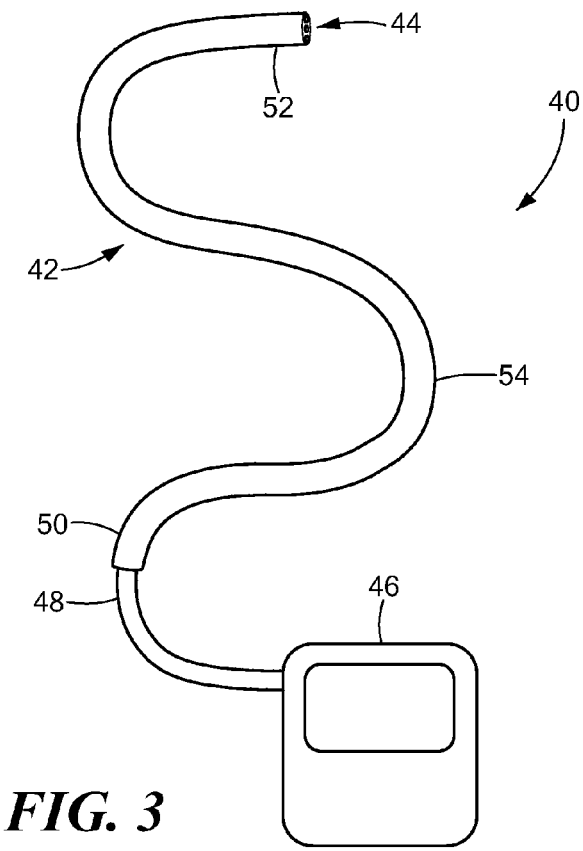
FIG. 3 is an embodiment of a medical device constructed in accordance with the principles of the present invention.

Referring now to the drawing figures in which like reference designations refer to like elements, an embodiment of a medical system 40 constructed in accordance with principles of the present invention is shown in FIG. 3. The medical system 40 generally includes a catheter 42 having an optical array 44 coupled to a spectrometer 46 through an umbilical system 48.

The catheter 42 comprises a proximal portion 50, a distal portion 52 and an elongate flexible tubular body 54. The distal portion 52 of the catheter 42 may include an ablation element, a balloon and/or one or more sensors to monitor various parameters including for example pressure, temperature, flow rate, volume, or the like. The catheter 42 may also optionally include one or more lumens disposed within the elongate body, thereby providing mechanical, electrical, and/or fluid communication between the proximal portion 50 and the distal portion 52 of the catheter. The catheter 42 may be made of a flexible material and may be typically 80 cm to 100 cm long, but may optionally be shorter or longer. The body 54 of the catheter 42 may be typical of catheters for use in transseptal procedures that include introducing the distal portion of the catheter into the right atrium of the heart and proceeding into the left atrium by puncturing the interatrial septum. All or a portion of the catheter 42 may optionally be comprised of radiopaque material or may include one or more radiopaque markers.

The umbilical 48 may be a bundle of optical fibers or electrical wires placing the spectrometer 46 in communication with the optical array 44. Other umbilicals may optionally be used to operate other sensors or other devices, for example an ablation device. The spectrometer 46 may include processors that may analyze optical data, for example the wavelengths and amplitudes of the emitted light and the wavelengths and amplitudes of detected reflected light at particular wavelengths. The spectrometer 46 may provide one or more graphs of the data or may optionally perform mathematical analyses on the data, as explained in more detail below.

Figure 4:
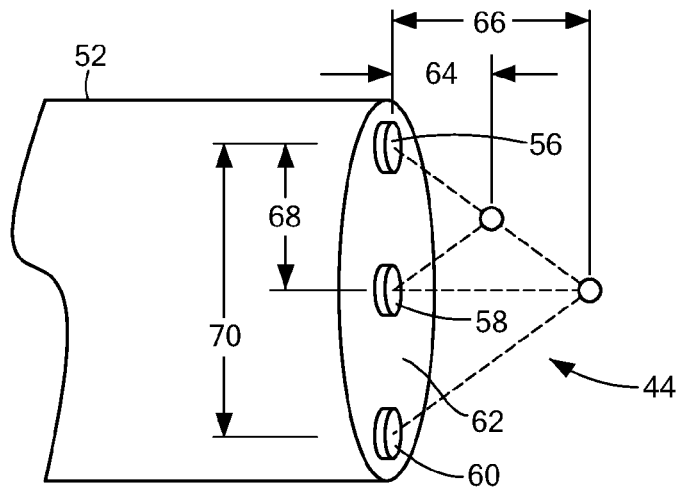
FIG. 4 is an enlarged view of the optical array of the medical device of FIG. 3.

Referring now to FIG. 4, the optical array 44 is shown in more detail. The optical array 44 includes an emitter 56 for emitting light directed at tissue surrounding and in front of the distal portion 52 of the catheter 42 of FIG. 3. The emitter 56 may be composed of any device suitable for emitting light, for example a light-emitting-diode or similar device. Optionally, the emitter 56 may be a plate or window, comprised of for example glass, acrylic or other transparent material, in communication with an optical fiber that provides light to the emitter 56. The emitter 56 also may simply be the end of an optical fiber. The light emitted by the emitter 56 may be a broad band of light ranging over several wavelengths or may be of selected discrete wavelengths. The emitter 56 may further include a filter (not shown) for filtering the type of light emitted. Optionally, a plurality of emitters may be used.

The optical array 44 also includes two receivers 58 and 60 for detecting light reflected from adjacent tissue(s). As used herein, the term "tissue" refers generally to any tissue within the human body, such as muscle, fibrous tissue, blood, and others. The receivers 58 and 60 may be comprised of any device known to detect light. The receivers may be a plate or window, comprised of for example glass, acrylic, or other transparent material, in communication with an optical fiber and transmitting detected light to the optical fiber. The receivers 58 and 60 may also simply be the end of an optical fiber. The receivers 58 and 60 may optionally be devices that measure various parameters of detected light, for example wavelengths, amplitudes and/or other parameters, and generate an electrical or other signal containing information about the measured parameters. The receivers 58 and 60 may detect a broad range of wavelengths or only selected wavelengths, and may optionally include filters for selecting which wavelengths are detected.

The optical array 44 may be located on the face plate 62 positioned at the distal portion 52 of the catheter 42. The face plate 62 may be substantially planar and optionally may be substantially perpendicular to the longitudinal axis of the catheter 42. Optionally, the distal portion 52 of the catheter 42 may include a radiopaque marker, not shown, which may be on the face plate 62. Optionally, all or part of the catheter 42 may be composed of a radiopaque material.

FIG. 4 also illustrates the relationship between the distance between the emitter 56 and the receivers 58 and 60 and their respective target depths of penetration 64 and 66. As used herein, the term "target depth" refers generally to the penetration distance of light from emitters to within tissue where the main spatial distribution of light reaches a maximum depth. There is a linear correlation between the distance between an emitter and a receiver and a distance light travels into a tissue in order to be detected. The optical array 44 therefore may acquire spectral information from tissue(s) at different distances from the optical array because it has two receivers that are at different distances from the emitter. The distance 68 separates the emitter 56 and the receiver 58 from each other. As a result, any light detected by the receiver 58 travels to the depth of penetration 64 or further. Light reflected from a point closer to the optical array 44 may not be detected by receiver 58.

Similarly, reflected light detected by the receiver 60 travels at least to the target depth of penetration 66. Because the distance 70 separates the emitter 56 and the receiver 60 from one another, any light detected by receiver 60 travels at least to the target depth of penetration 66. Where the distance 70 is twice the distance 68, the depth of penetration 66 for the receiver 60 will be approximately twice the distance 64 for the receiver 58. Incorporation of the emitter 56 and the receivers 58 and 60 into the face plate 62 may allow these distances to remain constant.

While the correlation between the distance between an emitter and a receiver and the depth of penetration may be generally linear, the actual depth of penetration for a given distance between an emitter and receiver may be affected by a variety of factors and may be determined empirically. The correlation may depend on the wavelengths used, the geometry of the emitter and the receiver, the type of tissue, and other factors.

Figure 5:
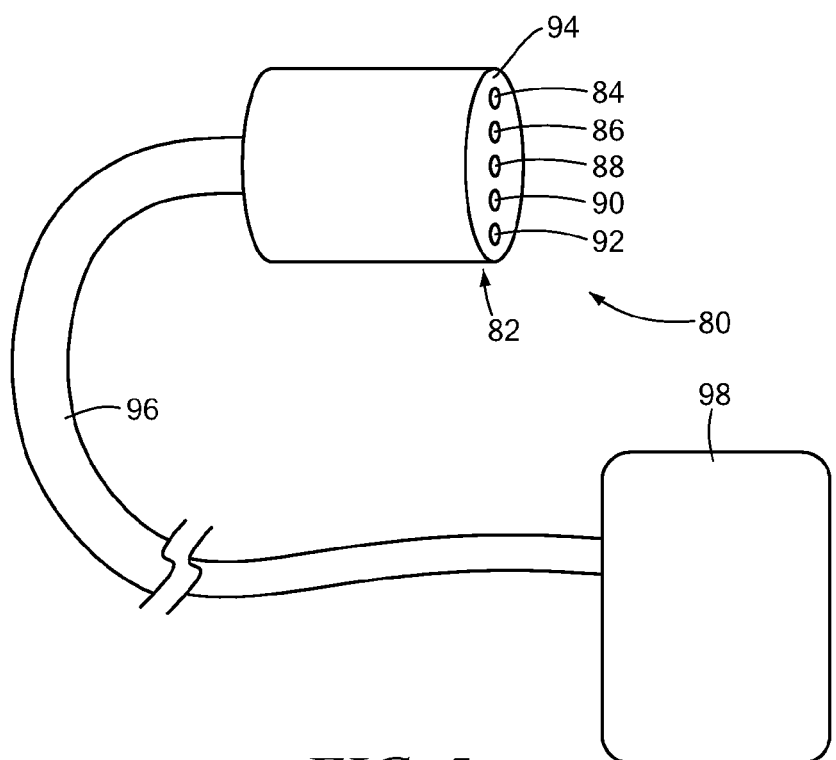
FIG. 5 is an alternative embodiment of a medical device constructed in accordance with the principles of the present invention.

Referring now to FIG. 5, an alternative medical device 80 has an optical array 82 including an emitter 84 and a series of four receivers 86, 88, 90 and 92 linearly arranged at increasing distances from the emitter 84. The optical array 82 may be insertable into the lumen of a catheter such that it may be removably placed at the distal portion of the catheter instead of as an integral component of the catheter itself. The optical array 82 may also include a face plate 94 into which the emitter 84 and the receivers 86, 88, 90 and 92 may be incorporated. An umbilical 96 connects the optical array 82 to a spectrometer 98 that may provide light to be emitted to the emitter 84 and may measure light detected by the receivers 86, 88, 90 and 92 in order to analyze the spectroscopic data collected. Optionally, the umbilical 96 may include electrical wires capable of transmitting signals from the emitter 84 and the receivers 86, 88, 90 and 92 to the spectrometer 98. Because all four receivers 86, 88, 90 and 92 are different distances from the emitter 84, they all observe light traveling to different depths of penetration.

Figure 6:
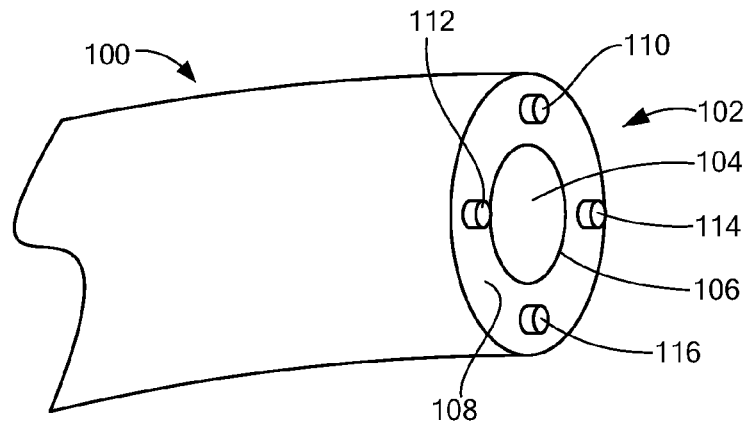
FIG. 6 is an alternative embodiment of an optical array constructed in accordance with the principles of the present invention.

Referring now to FIG. 6, a catheter 100 has an optical array 102 and a lumen 104 that extends its length and allows various instruments to be inserted into the catheter 100 such that they protrude from the lumen opening 106. For example, a piercing or puncturing instrument such as a needle may be passed through the lumen 104 and out of the opening 106 to facilitate puncturing of the fossa ovalis once it has been localized using the optical array 102. The puncturing instrument may then be withdrawn and replaced with an ablation or other instrument.

The optical array 102 of the catheter 100 may be located on an annular, planar face plate 108 surrounding the lumen opening 106. The face plate 108 may be flat and lie in a plane substantially perpendicular to the longitudinal axis of the catheter 100. The emitter 110 emits light of discrete wavelengths or a band of wavelengths. The receivers 112 and 114 may be equidistant from the emitter 110. The two receivers 112 and 114 may have the same depths of penetration. The receiver 116 may be farthest from the emitter 110 and allows the optical array 102 to gather spectroscopic data from regions farther from the face plate 108.

Figure 7:
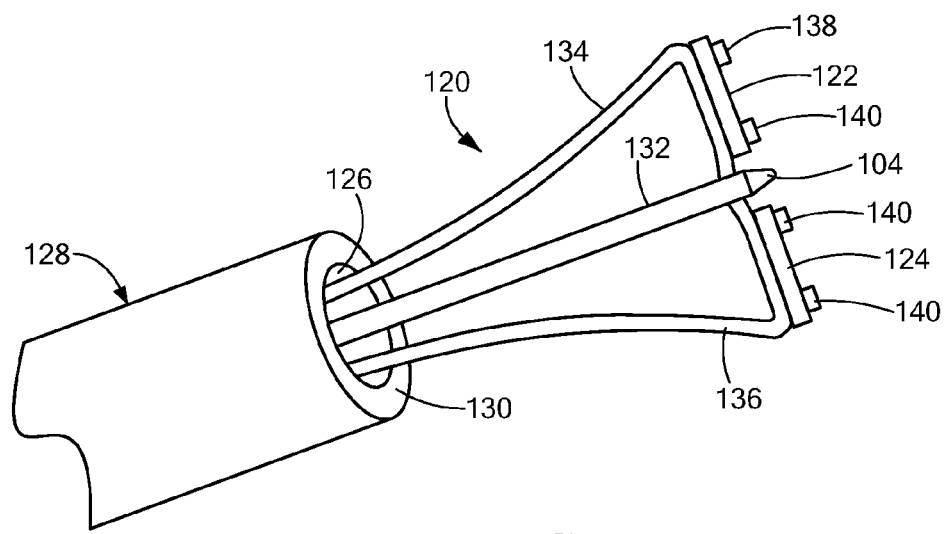
FIG. 7 is an alternative embodiment of an optical array constructed in accordance with the principles of the present invention.

Referring now to FIG. 7, an optical array 120 having two face plates 122 and 124 may be collapsed and inserted into a lumen 126 in a catheter 128. Once it has traversed the length of the catheter 128 and protrudes out at the distal portion 130 of the catheter 128, the optical array 120 may be expanded. The optical array 120 may be mounted on a wire 132 which supports the optical array 120 and may have a radiopaque marker 104 to assist in observing the position of the optical array 120. The face plates 122 and 124 may be supported by the cables 134 and 136 respectively. The optical array 120 may be expanded so that the face plates 122 and 124 may be parallel and the emitter 138 and the receivers 140 all align in a single plane. By adjusting the cables 134 and 136, the face plates 122 and 124 may be adjusted such that they may not be parallel and/or not lie in the same plane.

Figure 8:
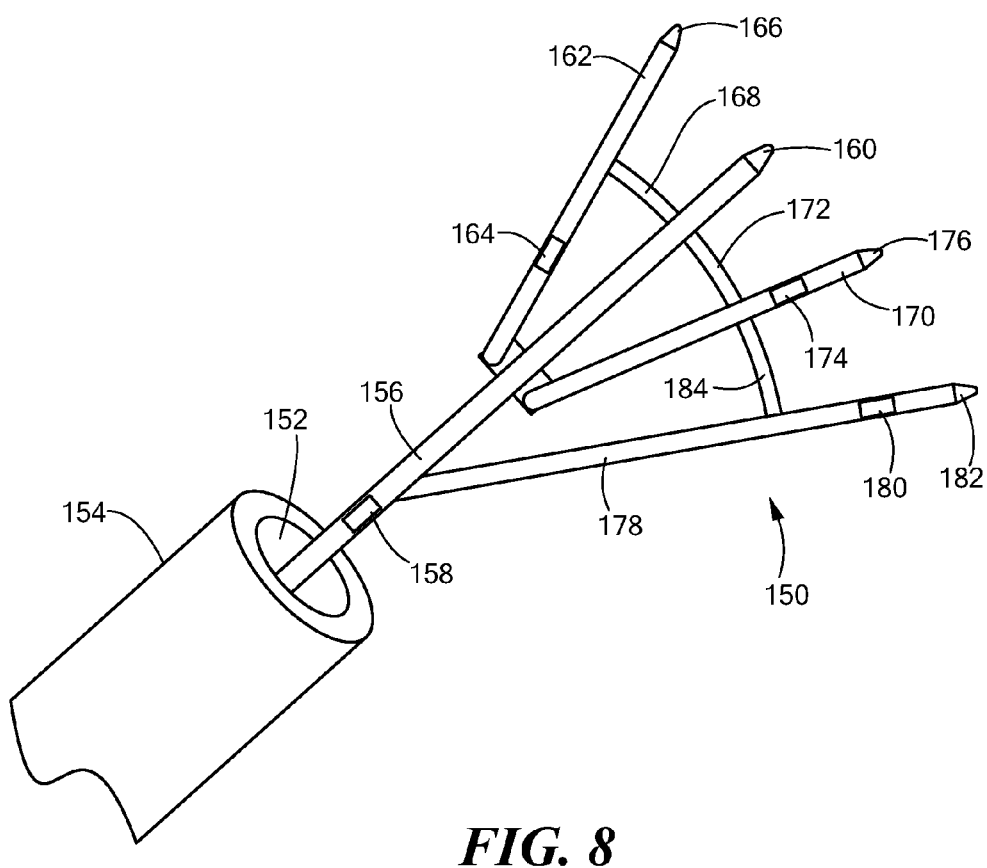
FIG. 8 is an alternative embodiment of an optical array constructed in accordance with the principles of the present invention.
Figure 9:
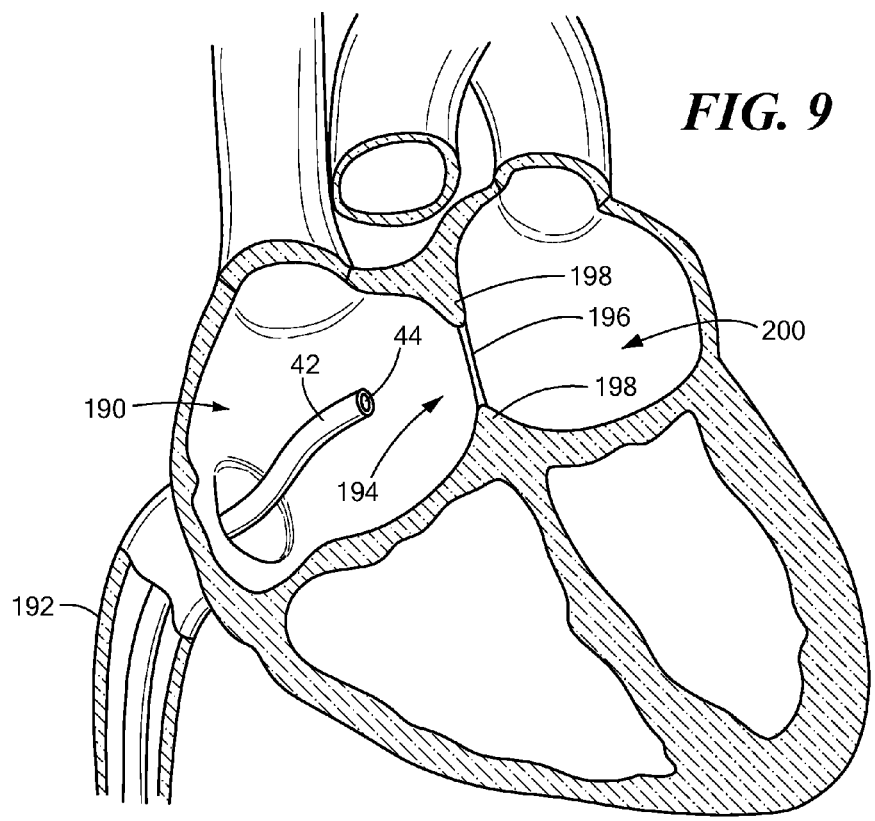
FIG. 9 is a perspective view of the medical device of FIG. 3 in a human heart.

Referring now to FIG. 8, an optical array 150 may be collapsed so that it may fit through the lumen 152 of the catheter 154. Upon exiting the lumen 152, the optical array 150 may be expanded using cables, not shown. The optical array 150 may be mounted on a wire 156 which may have a radiopaque marker 158 and a receiver 160. The expanding arm 162 also may have a radiopaque marker 164 and an emitter 166. Optionally, some or all of the optical array 150 may be comprised of a radiopaque material. The expanding arm 162 expands to a distance from the wire 156 determined by the length of the cable 168. Similarly, the expanding arm 170 expands to a distance from the wire 156 determined by the length of the cable 172, and includes a radiopaque marker 174 and a receiver 176. The expanding arm 178 includes a radiopaque marker 180 and a receiver 182 and expands to a predetermined distance determined by the length of the cable 184. The expanding arms 162, 170 and 178 each have a specific length such that when expanded, the emitter 166 and the receivers 160, 176 and 182 all lie in the same plane. By adjusting the lengths of the cables 138, 142 and 184, the plane in which the receivers lie may be warped so that it may be concave or convex. Additional expanding arms may optionally be included to provide additional receivers. The optical array 150 does not include a face plate. By using expanding arms that when expanded place the emitter 166 and receivers 160, 176 and 182 at known positions relative to each other, their respective depths of penetration may be determined.

Referring now to FIGS. 9-13, in an exemplary method of use, the medical system 40 of FIG. 3 may be used to acquire optical information for a targeted tissue area. Specifically, the medical system 40 may be used to localize the fossa ovalis during a trans-septal procedure. Catheter 42 may be introduced into the right atrium 190 after being routed through the vascular system, for example, through the inferior vena cava 192. The superior vena cava may optionally be utilized for jugular or subclavian insertions. Traversing the vasculature and positioning of the optical array 44 may be aided by imaging techniques (fluoroscopy, etc.). Once in the vicinity of the targeted tissue, the optical array 44 may be advanced at least partially into contact with the atrial wall, of which the interatrial septum 194 is a portion. The interatrial septum 194, comprised of the fossa ovalis 196 and muscular tissue 198, separates the right atrium 190 and the left atrium 200. Once the optical array 44 at the distal region of the catheter 42 is in the right atrium 190, the catheter may be guided such that the optical array 44 abuts the interatrial wall. The distal portion of the catheter moves about the interatrial wall of the right atrium 190 as the optical array 44 emits light and detects the absorption spectra of the tissue(s) it encounters. When an absorption spectrum consistent with the fossa ovalis 196, such as the spectrum 197 in FIG. 10, the catheter 42 may remain in that location while the fossa ovalis 196 is punctured.

Figure 10:
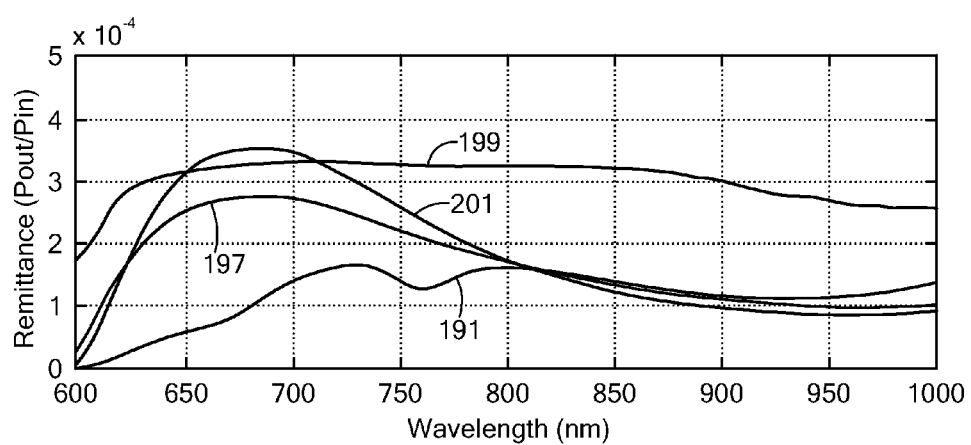
FIG. 10 a graph of absorption spectra of various tissues found within the human heart.

FIG. 10 shows the spectra observed by the optical array 44 when it encounters different tissues within the heart. The spectrum 191 characteristic of deoxygenated blood may be observed by the optical array 44 while traveling through the vena cava and into the right atrium. The spectrum 201 is the absorption spectra of the oxygenated blood of the left atrium. The spectrum 197 may be observed when the optical array 44 abuts the fossa ovalis and is an attenuated version of the oxygenated blood spectrum 201. The fossa ovalis spectrum 197 has the negative curvature and increased remittance between 600 nm and 805 nm found in the spectrum 201, but the remittance may be lowered across the length of the spectrum, resulting from travel through the fossa ovalis 196. Actual spectra observed at a fossa ovalis may be more or less attenuated than spectrum 197 shown here, but may generally retain the curvature and slope of oxygenated blood. Muscular tissue may generally have a spectrum similar to spectrum 199, reflecting a substantial amount of light directed at it.

Figure 11:
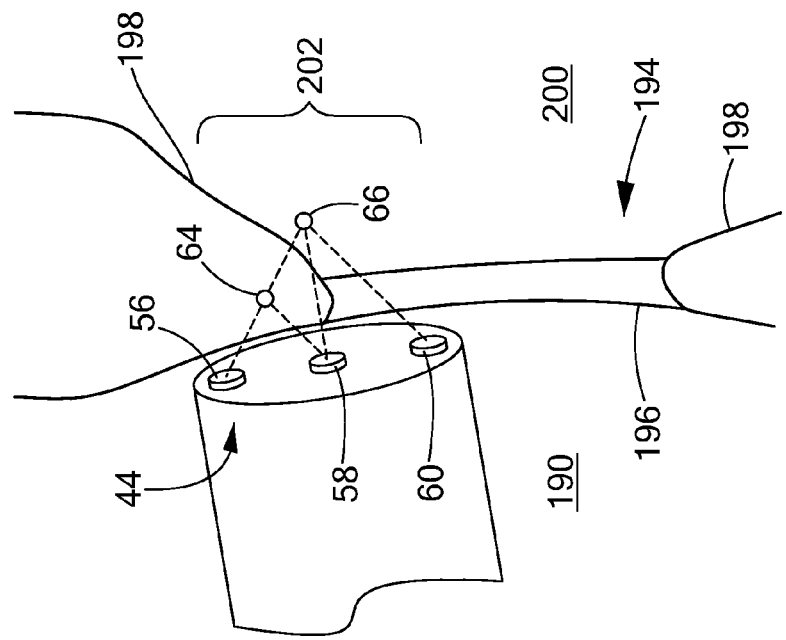
FIG. 11 is an enlarged view of the optical array of FIG. 4 abutting an interatrial septum.

Referring now to FIG. 11, the optical array 44 abuts against a location 202 on the interatrial septum 194. The location 202 includes both the muscular tissue 198 and the fibrous fossa ovalis 196. The depth of penetration 64 may be located within the muscular tissue 198 and the spectra detected by the receiver 58 may be indicative of muscular tissue, similar to the spectrum 199 in FIG. 10. The depth of penetration 66, however, may be located in the left atrium 200 and therefore the spectrum detected by the receiver 60 may be similar to an attenuated left atrium blood spectra similar to the spectrum 197 in FIG. 10, indicating the fossa ovalis. The absorption spectrum detected by the receiver 60 may be weak as most of the light may be unable to penetrate the muscular tissue 198. The receivers do not both detect a spectrum indicating the fossa ovalis, indicating that the optical array 44 likely does not completely abut the fossa ovalis 196. The optical array 44 may then be repositioned in a new location in order to determine whether a location exists at which both receivers detect spectra similar to the spectrum 197 indicative of the fossa ovalis.

Figure 12:
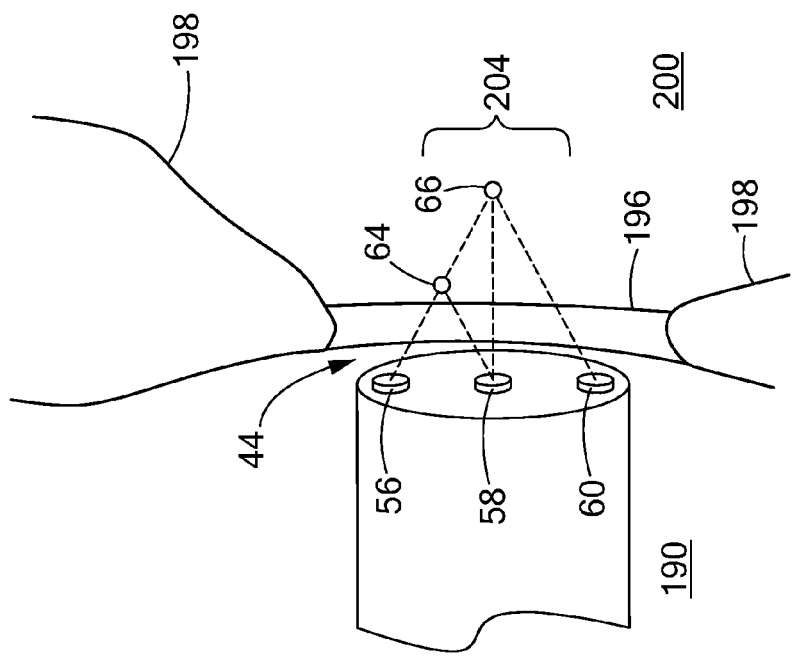
FIG. 12 is an enlarged view of the optical array of FIG. 4 abutting the fossa ovalis of an interatrial septum.

Referring now to FIG. 12, the optical array 44 abuts against a location 204 on the fossa ovalis 196. As a result, both depths of penetration 64 and 66 are within the left atrium 200 and therefore both receivers 58 and 60 detect spectra having the characteristics of oxygenated blood similar to the spectra 197 and 201 in FIG. 10, indicative of the fossa ovalis 196. By moving the optical array 44 across the atrial wall as shown in FIGS. 11 and 12, the fossa ovalis 196 may be accurately localized. The change in spectra observed by the receivers is not instantaneous, but rather the spectra change slowly as the optical array is moved across the interatrial septum. The optical array 44 may therefore be moved about the interatrial septum until a spectrum is observed by all of the receivers that has the most similarity to the spectrum 201 of oxygenated blood, and may appear similar to the attenuated fossa ovalis spectrum 197.

FIG. 13 shows the optical array 44 in contact with a relatively thick fossa ovalis 206. The thicknesses of fossa ovali vary significantly between individuals. When an optical array 44 encounters a thick fossa ovalis 206, the light reflected from the depth of penetration 64 may not be within the left atrium 208. As a result, the spectrum of light detected by the receiver 58 may be relatively flat and similar to the spectrum 199 in FIG. 10, inconsistent with the fossa ovalis. Were the receiver 58 the only receiver, then the fossa ovalis 180 may not be localized. However, the receiver 60 has a greater depth of penetration 66, allowing it to detect the blood of the left atrium 208. As a result, the receiver 60 detects a spectrum similar to that of the spectrum 197 in FIG. 10, indicating the fossa ovalis. The optical array 44, by including two or more receivers, allows an operator to determine the presence of the fossa ovalis 206 despite its relative thickness. As an example, the measurements of the spectra may be similar or comparable to a weighted average between spectra 36 and 32, with weighting biased more towards spectra 32 for receiver 60, and the net spectra approaching that of 32 as the ratio of spacing over thickness increases. Due to the non-discrete nature and range of potential thicknesses of the fossa ovalis (or other targeted tissue), a clinically established threshold may be used to differentiate.

Referring now to FIG. 14, the optical array 82 of medical device 80 in FIG. 5 has four receivers, each a different distance from the emitter 84. The receiver 86 has a depth of penetration 210. The receiver 88 has a depth of penetration 212. The receiver 90 has a depth of penetration 214. The receiver 92 has a depth of penetration 216. This arrangement of receivers allows a determination of the thickness of the fossa ovalis 218. The receivers 86 and 88 have depths of penetration 210 and 212 that may be less than the thickness of the fossa ovalis 218 in this example and will thus detect spectra similar to the spectrum 199 of FIG. 10. The receivers 90 and 92, on the other hand, have depths of penetration 214 and 216 that may be greater than the thickness of the fossa ovalis 218 and may detect spectra more similar to the spectrum 197 of FIG. 10. From this, an operator may determine that the thickness of the fossa ovalis 218 may be greater than the depth of penetration 212 but less than the depth of penetration 214. Knowledge of the thickness of the fossa ovalis 218 may be beneficial in allowing an operator to estimate the amount of force that must be applied to a puncturing instrument. By applying a correct amount of force to the puncturing instrument, the possibility of using too much force and damaging tissue within the left atrium is minimized.

Because the actual spectra observed may not be as clearly distinct as the spectra 191, 197 and 199 shown in FIG. 10, various algorithms may be used to estimate that actual thickness of the fossa ovalis. That is, the spectra observed by receiver 88 and receiver 90 may have more subtle differences than the clear differences between spectra 197 and 199. Empirically obtained data may be used to compare to actual data obtained using the optical array in order to accurately determine the thickness of a fossa ovalis. One such example of determining the desired location may include estimating the thickness of the fossa ovalis wall based on a projection from 1 or more measurements in conjunction with clinically measured empirical data. For example, the equation $Sm=(1-f) \times Sfo + f \times Sla$ may be used to approximate the location and spectra characteristics, where "Sm" is the measured spectra, "Sfo" is an empirically determined characteristic spectrum of the fossa ovalis when the separation distance is less than half the fossa ovalis thickness, and "Sla" is the spectrum characteristic of the left atrium when the probe is in pure left atrium blood or the separation distance is several times greater than the fossa ovalis thickness. "f" is a scaling factor in the range of 0 to 1. Given "Sm" and predetermined clinical "Sfo" and "Sla" (for each separation distance), we may solve for "f" which may be empirically correlated to wall thickness for a given probe design and separation distance. A series of "f" values (denoted "fi") corresponding to multiple separation distances can improve the confidence in the thickness estimate over broader ranges.

Due to potentially widely varying offset shifts in the spectra amplitude, this exemplary approach may require normalizing the spectra by a discrete wavelength such as the isosbestic point, such that "Sm," "Sfo," "Sla" are each normalized by their respective values at wavelength of approximately 805 nm.

Multiple methods of analysis exist by which spectra detected may be characterized. For example, an optical array may detect reflected light at two wavelengths, one between 600 and 805 nm and one between 805 and 1000 nm. Specifically, the optical array may detect light at wavelengths of 660 nm and 940 nm. Remittance for each wavelength is calculated by dividing the amplitude of light reflected by the amplitude of light emitted at each wavelength. As can be seen in FIG. 10, deoxygenated blood absorbs more light between 600 nm and 805 nm, illustrated by the spectrum 30, while oxygenated blood reflects more light in this band, illustrated by spectra 32 and 34.

Oxygenated and deoxygenated blood share an isobestic point at 805 nm. At wavelengths above the isobestic point oxygenated and deoxygenated blood have similar but opposite spectral responses compared with the responses the within 600 to 805 nm range. Thus, by comparing the remittance values detected at 660 nm and 940 nm, for example by dividing the remittance at 660 nm by the remittance at 940 nm to generate a remittance ratio, the percentage of oxygen saturation of blood may be accurately determined. A high remittance ratio indicates oxygenated blood as detected. Such a reading may indicate that an optical array is proximate to the fossa ovalis.

The above described technique of normalizing reflectance at one characteristic wavelength using reflectance at an isobestic or constant wavelength may be used to identify regions within the body based upon blood oxygenation, but may also be used to identify any region or tissue(s) by characteristic wavelengths.

Other methods may be used to identify the characteristic spectra of different tissue(s) including blood. For example, the entire spectra between 600 nm and 1000 nm can be detected using the optical array and displayed on a screen for an operator to view. Alternatively, discrete wavelengths can be measured using either a broad band emission or emission only of the light to be detected.

For example, light at wavelengths between 700 and 800 nm may be detected. In this region, oxygenated left atrial blood exhibits a substantially constant negative slope, as shown in the spectra 197 and 201 in FIG. 10. The muscle of the interatrial septum exhibits a flat spectrum in this region while deoxygenated, right atrial blood exhibits a zig-zag spectrum, dipping markedly at 760 nm. Thus, the fossa ovalis may be localized by identifying the region of the interatrial septum in the right atrium where an optical array reads a spectrum having a relatively constant, negative slope between 700 and 800 nm. The region of the atrial wall having the most negative slope in this wavelength range may be the fossa ovalis.

There are several known mathematical methods suitable for accurately identifying these different spectra. For another example, the spectra 197 and 201 in FIG. 10 are concave down in the range of 600 nm to 760 nm. Thus, these spectra have a negative second derivative, or curvature. As used herein, the term curvature refers to the second derivative of a line and is a measure of the rate at which the slope of a line changes over a range. The spectrum 191 has a relatively steady positive slope in this region, resulting in a curvature close to 0. A spectrometer connected to the optical array could first measure the remittance at three or more points in this range, calculate the slopes between adjacent points, and calculate the curvature. The fossa ovalis may be localized by identifying the region of the interatrial septum having the most negative curvature.

A spectrometer may perform some or all of these calculations on reflected light detected by a receiver to identify the region of the septum at which the most left atrial, oxygenated blood is detected. This region may generally be the fossa ovalis. Any of these above techniques may be used to identify different tissues of within the right atrium so that the fossa ovalis may be identified. Once the fossa ovalis is found, a piercing apparatus may be introduced so that one or more medical devices may enter the left atrium.

The optical arrays described above may be used to identify and characterize tissue(s) other than the anatomical localization of the fossa ovalis. For example, other tissues, both normal and those possessing inherent physiological and pathological conditions of interest, having characteristic spectra may be identified using the above methods and systems described. Identification and characterization of particular tissues adjacent to a medical device aid in a variety of medical procedures.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system for identifying the location of an intravascular catheter within a patient's body, comprising:
   an intravascular catheter;
   an optical array including:
      a light emitter adapted to emit light toward at least one tissue within the patient's body, the light including a plurality of wavelengths; and
      a plurality of receivers, each of the plurality of receivers configured to detect at least two of the plurality of wavelengths emitted by the light emitter and reflected back to the plurality of receivers, wherein two or more of the plurality of receivers are each positioned at different distances from the emitter;
   a face plate coupled to a distal portion of the intravascular catheter, the emitter and each of the plurality of receivers being located on the face plate; and
   a spectrometer in communication with the emitter and the plurality of receivers, the spectrometer including one or more processors programmed to:
      calculate remittance values for the at least two wavelengths of light detected by each of the plurality of receivers;
      calculate a relationship between the remittance values; and
      determine the location of the intravascular catheter relative to a fossa ovalis based at least in part on the relationship between the remittance values.

2. The medical system of claim 1, wherein the plurality of receivers comprises two receivers.

3. The medical system of claim 1, wherein the plurality of receivers comprises four receivers.

4. The medical system of claim 1, wherein the one or more processors are programmed to determine a depth of an area of target tissue based at least in part on optical data received from one or more of the plurality of receivers.

5. The medical system of claim 1, wherein the one or more processors are programmed to calculate the relationship between the remittance values by dividing the remittance value of a first wavelength by the remittance value of a second wavelength for each of the plurality of receivers.

6. The medical system of claim 5, wherein each of the plurality of receivers is adapted to receive the first wavelength and the second wavelength, the first wavelength being between 600 nm and 805 nm and the second wavelength being between 805 nm and 1000 nm.

7. The medical system of claim 6, wherein the first wavelength is 660 nm and the second wavelength is 940 nm.

8. The medical system of claim 1, wherein the one or more processors are programmed to calculate the relationship between the remittance values, the relationship including a slope calculated for at least two remittance values calculated at each of the two of more receivers, the location of the intravascular catheter being based at least in part on the slope.

9. The medical system of claim 1, wherein the one or more processors are programmed to calculate the relationship between the remittance values, the relationship including a curvature calculated for the at least two wavelengths of light detected by the plurality of receivers, the location of the intravascular catheter being based at least in part on the curvature.

* * * * *